(12) United States Patent
Matsuzaki et al.

(10) Patent No.: US 8,580,836 B2
(45) Date of Patent: Nov. 12, 2013

(54) PLANT DISEASE CONTROL COMPOSITION AND METHOD OF CONTROLLING PLANT DISEASE

(75) Inventors: Yuichi Matsuzaki, Toyonaka (JP); Hiroshi Sakaguchi, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/806,469

(22) PCT Filed: Jun. 20, 2011

(86) PCT No.: PCT/JP2011/064604
§ 371 (c)(1),
(2), (4) Date: Dec. 21, 2012

(87) PCT Pub. No.: WO2011/162397
PCT Pub. Date: Dec. 29, 2011

(65) Prior Publication Data
US 2013/0096174 A1  Apr. 18, 2013

(30) Foreign Application Priority Data
Jun. 24, 2010  (JP) .................................. 2010-143553

(51) Int. Cl.
*A61K 31/415* (2006.01)
*C07D 231/10* (2006.01)

(52) U.S. Cl.
USPC ....................................... 514/406; 548/374.1

(58) Field of Classification Search
USPC ....................................... 514/406; 548/374.1
See application file for complete search history.

(56) References Cited

U.S. PATENT DOCUMENTS

| | | |
|---|---|---|
| 4,742,074 A | 5/1988 | Nishida et al. |
| 4,877,441 A | 10/1989 | Mori et al. |
| 5,004,816 A | 4/1991 | Mori et al. |
| 5,093,347 A | 3/1992 | Graneto et al. |
| 5,521,317 A | 5/1996 | Briner |
| 5,728,869 A | 3/1998 | Briner |

FOREIGN PATENT DOCUMENTS

| | | |
|---|---|---|
| JP | 1-211568 A | 8/1989 |
| JP | 2-131481 A | 5/1990 |
| JP | 6-505252 A | 6/1994 |
| JP | 7-215921 A | 8/1995 |
| WO | WO 86/02641 A1 | 5/1986 |

OTHER PUBLICATIONS

International Preliminary Report on Patentability for International Patent Application No. PCT/JP2011/064604, dated Dec. 28, 2012.
International Search Report mailed Aug. 9, 2011, issued in PCT/JP2011/064604.
Written Opinion of the International Searching Authority mailed on Aug. 9, 2011, issued in PCT/JP2011/064604.

*Primary Examiner* — Samantha Shterengarts
(74) *Attorney, Agent, or Firm* — Birch, Stewart, Kolasch & Birch, LLP

(57) ABSTRACT

A plant disease control composition comprising a carboxamide compound represented by formula (I) whose enantiomer ratio R form/S form of the carboxamide compound is 80/20 or more has an excellent plant disease controlling activity.

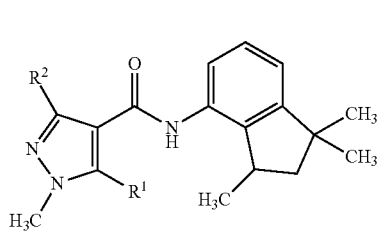

(I)

12 Claims, No Drawings

PLANT DISEASE CONTROL COMPOSITION AND METHOD OF CONTROLLING PLANT DISEASE

TECHNICAL FIELD

The present invention relates to a plant disease control composition and a method of controlling a plant disease.

BACKGROUND ART

A plant disease control composition and a method of controlling a plant disease using the same are known (e.g., patent WO 86/02641 and WO 92/12970).

DISCLOSURE OF INVENTION

The object of the present invention is to provide a composition having an excellent control effect on a plant disease.

The present inventor has investigated to find a composition having an excellent control effect on a plant disease and resultantly found that a composition comprising a carboxamide compound represented by formula (I) described below in which both an optically active R form and an optically active S form of the carboxamide compound are present in a prescribed enantiomer ratio has an excellent control effect on a plant disease, leading to completion of the present invention.

That is, the present invention is as described below.

[1] A plant disease control composition comprising a carboxamide compound represented by formula (I):

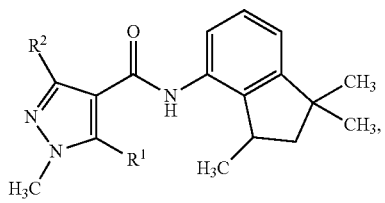

(I)

wherein
$R^1$ represents hydrogen or methyl,
$R^2$ represents methyl, difluoromethyl or trifluoromethyl,
and the enantiomer ratio R form/S form of the carboxamide compound is 80/20 or more.

[2] The plant disease control composition according to [1], wherein the enantiomer ratio R form/S form of the carboxamide compound is 90/10 to 10000/1.

[3] The plant disease control composition according to [1], wherein the enantiomer ratio R form/S form of the carboxamide compound is 95/5 to 10000/1.

[4] The plant disease control composition according to [1], wherein the enantiomer ratio R form/S form of the carboxamide compound is 98/1 to 1000/1.

[5] The plant disease control composition according to any one of [1] to [4], wherein $R^1$ is methyl and $R^2$ is methyl in formula (I).

[6] The plant disease control composition according to any one of [1] to [4], wherein $R^1$ is hydrogen and $R^2$ is difluoromethyl in formula (I).

[7] The plant disease control composition according to any one of [1] to [4], wherein $R^1$ is hydrogen and $R^2$ is trifluoromethyl in formula (I).

[8] A method of controlling a plant disease comprising a step of treating a plant or a soil where a plant grows with an effective amount of the plant disease control composition according to any one of [1] to [7].

[9] A carboxamide compound represented by formula (I-R):

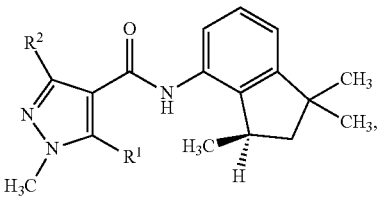

(I-R)

wherein
$R^1$ represents hydrogen or methyl,
$R^2$ represents methyl, difluoromethyl or trifluoromethyl.

[9-2] The carboxamide compound according to [9], wherein the carboxamide compound is an essentially pure R isomer of the absolute configuration.

[9-3] The carboxamide compound according to [9], wherein the enantiomer ratio R form/S form of the carboxamide compound is 80/20 or more.

[10] The carboxamide compound according to [9], wherein $R^1$ is methyl and $R^2$ is methyl.

[11] The carboxamide compound according to [9], wherein $R^1$ is hydrogen and $R^2$ is difluoromethyl.

[12] The carboxamide compound according to [9], wherein $R^1$ is hydrogen and $R^2$ is trifluoromethyl.

In the present invention, "the enantiomer ratio R form/S form of the carboxamide compound is 80/20 or more" means the carboxamide compound of an R-rich isomer containing 80% or more R isomer based on the RS mixture.

MODE OF CARRYING OUT THE INVENTION

The plant disease control composition of the present invention (hereinafter, may be referred to as the inventive composition) is a plant disease control composition comprising a carboxamide compound represented by formula (I):

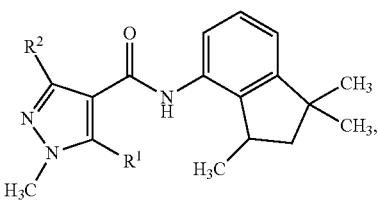

(I)

wherein $R^1$ and $R^2$ represent the same meaning as described above,
and the enantiomer ratio of a R form represented by formula (I-R)

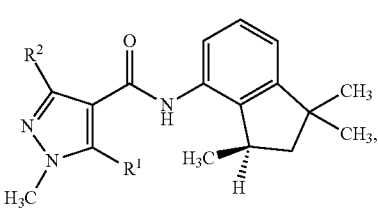

(I-R)

wherein R¹ and R² represent the same meaning as described above
to an S form represented by formula (I-S)

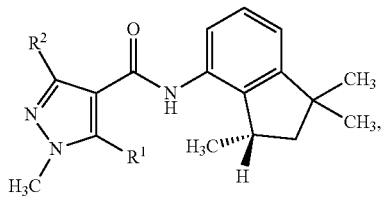

(I-S)

wherein R¹ and R² represent the same meaning as described above,
based on the asymmetric carbon in the carboxamide compound, is 80/20 (=R form/S form) or more.

The carboxamide compound represented by formula (I)

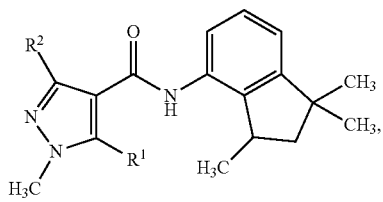

(I)

wherein R¹ and R² represent the same meaning as described above,
and the enantiomer ratio R form/S form is 80/20 or more (hereinafter, referred to as the present carboxamide compound) used in the present invention is obtained, for example, by the following production methods.

Production Method 1

The present carboxamide compound can be produced by reacting a compound (II) and a compound (III) in which the enantiomer ratio R form/S form is 80/20 or more in the presence of a dehydration-condensing agent.

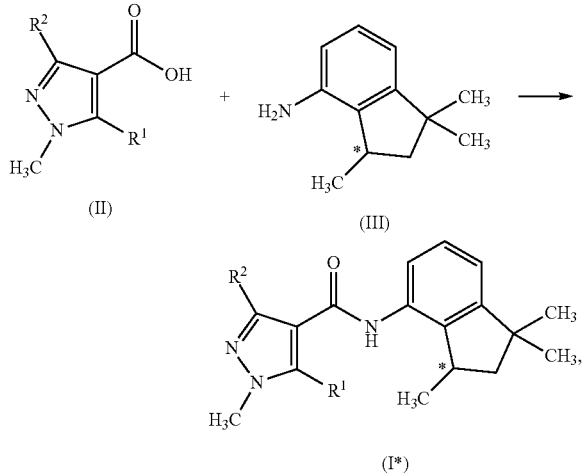

wherein R¹ and R² represent the same meaning as described above. The enantiomer ratio based on an asymmetric carbon represented by * is 80/20 (=R form/S form) or more.

The reaction is carried out usually in the presence of a solvent.

Examples of the solvent used in the reaction include ethers such as tetrahydrofuran (hereinafter, may be referred to as THF), ethylene glycol dimethyl ether, and tert-butyl methyl ether (hereinafter, may be referred to as MTBE); aliphatic hydrocarbons such as hexane, heptane, and octane; aromatic hydrocarbons such as toluene, and xylene; halogenated hydrocarbons such as chlorobenzene; esters such as butyl acetate, and ethyl acetate; nitriles such as acetonitrile; acid amides such as N,N-dimethylformamide; sulfoxides such as dimethyl sulfoxide; nitrogen-containing aromatic compounds such as pyridine; and mixtures thereof.

The dehydration-condensing agent used in the reaction includes carbodiimides such as 1-ethyl-3-(3-dimethylaminopropyl)carbodiimide hydrochloride, and 1,3-dicyclohexylcarbodiimide; and (benzotriazol-1-yloxy)tris(dimethylamino)phosphonium hexafluorophosphate and the like.

The compound (III) is used in a proportion of usually 0.5 to 3 mol and the dehydration-condensing agent is used in a proportion of usually 1 to 5 mol, with respect to 1 mol of the compound (II).

The reaction temperature of the reaction is usually in the range of −20° C. to 140° C., and the reaction time thereof is usually in the range of 1 to 24 hours.

After completion of the reaction, when a solid is deposited after adding water to the reaction mixture, the present carboxamide compound can be isolated by filtration, and when a solid is not deposited, the present carboxamide compound can be isolated by carrying out post treatment operations such as extraction of the reaction mixture with an organic solvent, drying of the organic layer and concentration thereof. The isolated present carboxamide compound can also be further purified by chromatography, re-crystallization and the like.

(Production Method 2)

The present carboxamide compound can also be produced by reacting a compound (IV) and a compound (III) in which the enantiomer ratio R form/S form is 80/20 or more in the presence of a base.

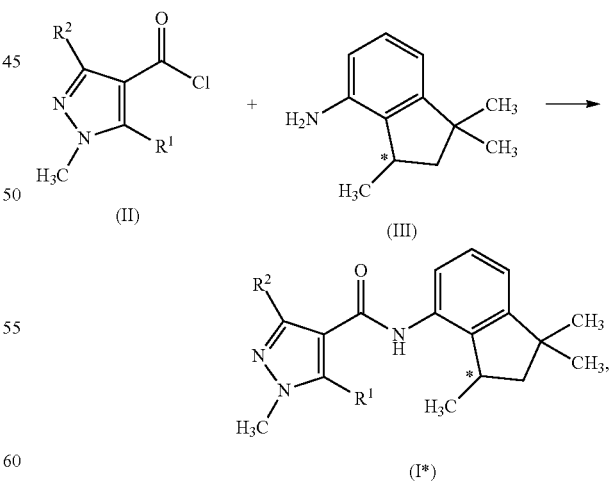

wherein R¹ and R² represent the same meaning as described above. The enantiomer ratio based on an asymmetric carbon represented by * is 80/20 (=R form/S form) or more.

The reaction is carried out usually in the presence of a solvent.

Examples of the solvent used in the reaction include ethers such as THF, ethylene glycol dimethyl ether, and MTBE; aliphatic hydrocarbons such as hexane, heptane, and octane; aromatic hydrocarbons such as toluene, and xylene; halogenated hydrocarbons such as chlorobenzene; esters such as butyl acetate, and ethyl acetate; nitriles such as acetonitrile; and mixtures thereof.

The base used in the reaction includes alkali metal carbonates such as sodium carbonate, and potassium carbonate; tertiary amines such as triethylamine, and diisopropylethylamine; nitrogen-containing aromatic compounds such as pyridine, and 4-dimethylaminopyridine; etc.

The compound (III) is used in a proportion of usually 0.5 to 3 mol and the base is used in a proportion of usually 1 to 5 mol, with respect to 1 mol of the compound (IV).

The reaction temperature of the reaction is usually in the range of −20° C. to 100° C., and the reaction time thereof is usually in the range of 0.1 to 24 hours.

After completion of the reaction, when a solid is deposited after adding water to the reaction mixture, the present carboxamide compound can be isolated by filtration, and when a solid is not deposited, the present carboxamide compound can be isolated by carrying out post treatment operations such as extraction of the reaction mixture with an organic solvent, drying of the organic layer and concentration thereof, and the like. The isolated present carboxamide compound can also be further purified by chromatography, re-crystallization and the like.

The compound (III) in which the enantiomer ratio R form/S form is 80/20 or more as a reaction intermediate can be obtained, for example, by the following method.

Method (1): 4-amino-1,1,3-trimethylindane, in which the enantiomer ratio R form/S form is for example 30/70 to 80/20 is allowed to generate a diastereomer salt using an optically active carboxylic acid, then, the crystal, is separated, further if necessary, re-crystallization thereof is performed, to obtain a diastereomer salt. The resultant diastereomer salt is decomposed with a base such as sodium hydroxide, to obtain a compound (III) in which the enantiomer ratio R form/S form is 80/20 or more.

Method (2): 4-amino-1,1,3-trimethylindane in which the enantiomer ratio R form/S form is for example 30/70 to 80/20, is made optical resolution by using a column for optical isomer separation using an optically active material as a filler component, to obtain a compound (III) in which the enantiomer ratio R form/S form is 80/20 or more.

Examples of the present carboxamide compound are as follows.

A carboxamide compound of formula (I) in which the enantiomer ratio R form/S form is 80/20 or more;

A carboxamide compound of formula (I) in which the enantiomer ratio R form/S form is from 90/10 to 10000/1;

A carboxamide compound of formula (I) in which the enantiomer ratio R form/S form is from 95/5 to 10000/1;

A carboxamide compound of formula (I) in which the enantiomer ratio R form/S form is from 98/1 to 1000/1.

Examples of the optically active material of the carboxamide compound represented by formula (I) include the following materials A carboxamide compound of formula (I-R) in which $R^1$ is hydrogen;

A carboxamide compound of formula (I-R) in which $R^1$ is methyl;

A carboxamide compound of formula (I-R) in which $R^2$ is methyl;

A carboxamide compound of formula (I-R) in which $R^2$ is difluoromethyl;

A carboxamide compound of formula (I-R) in which $R^2$ is trifluoromethyl;

A carboxamide compound of formula (I-R) in which $R^1$ is methyl and $R^2$ is methyl;

A carboxamide compound of formula (I-R) in which $R^1$ is hydrogen and $R^2$ is difluoromethyl;

A carboxamide compound of formula (I-R) in which $R^1$ is hydrogen and $R^2$ is trifluoromethyl.

The inventive composition is a formulation, such as a fixing agent, dispersing agent, stabilizing agent and the like are added, and the mixture is prepared into a wettable powder, granular wettable powder, flowable formulation, granule, dry flowable formulation, emulsifiable concentrate, aqueous liquid formulation, oil solution, smoking agent, aerosol, or microcapsule, which the present carboxamide compound is mixed with a solid carrier, liquid carrier, gas carrier, surfactant and the like, if necessary, auxiliary agents. The inventive composition usually contains the present carboxamide compound in a weight ratio of usually 0.1 to 99%, preferably 0.2 to 90%.

Examples of the solid carrier include fine powders and granules composed of clays (for example, kaolin, diatomaceous earth, synthetic hydrated silicon oxide, Fubasami clay, bentonite, acid clay), talcs, other inorganic minerals (for example, sericite, quarts powder, sulfur power, activated carbon, calcium carbonate, hydrated silica), and examples of the liquid carrier include water; alcohols (for example, methanol, ethanol), ketones (for example, acetone, methyl ethyl ketone), aromatic hydrocarbons (for example, benzene, toluene, xylene, ethylbenzene, methylnaphthalene), aliphatic hydrocarbons (for example, n-hexane, kerosene), ketones (for example cyclohexanone) esters (for example, ethyl acetate, butyl acetate), nitriles (for example, acetonitrile, isobutylnitrile), ethers (for example, dioxane, diisopropyl ether), acid amides (for example, dimethylformamide, dimethylacetamide), halogenated hydrocarbons (for example, dichloroethane, trichloroethylene, carbon tetrachloride).

Examples of the surfactant include alkyl sulfates, alkyl sulfonates, alkyl aryl sulfonates, alkyl aryl ethers and polyoxyethylenated substances thereof, polyoxyethylene glycol ethers, poly-hydric alcohol esters, and sugar alcohol derivatives.

Examples of other auxiliary agents for formulation include fixing agents and dispersing agents, specifically, casein, gelatin, polysaccharides (for example, starch, gum Arabic, cellulose derivatives, alginic acid), lignin derivatives, bentonite, sugars, synthetic water-soluble polymers (for example, polyvinyl alcohol, polyvinylpyrrolidone, polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, and fatty acids or esters thereof.

The inventive composition can be used for protecting a plant from a plant disease.

Examples of plant diseases on which the inventive composition exerts a control effect include the following diseases.

Rice diseases: *Magnaporthe grisea, Cochliobolus miyabeanus, Rhizoctonia solani, Gibberella fujikuroi.*

Wheat diseases: *Erysiphe graminis, Fusarium* sp. (*F. graminearum, F. avenacerum, F. culmorum, Microdochium nivale*), *Puccinia* sp. (*P. striiformis, P. graminis, P. recondita, P. triticina*), *Micronectriella nivale, Typhula* sp., *Ustilago tritici, Tilletia caries, Pseudocercosporella herpotrichoides, Mycosphaerella graminicola, Stagonospora nodorum, Pyrenophora tritici-repentis.*

Barley diseases: *Erysiphe graminis, Fusarium* sp. (*F. graminearum, F. avenacerum, F. culmorum, Microdochium* nivale), *Puccinia* sp. (*P. striiformis*, *P. graminis*, *P. hordei*), *Ustilago nuda*, *Rhynchosporium secalis*, *Pyrenophora teres*, *Cochliobolus sativus*, *Pyrenophora graminea*, *Rhizoctonia solani*.

Corn diseases: *Ustilago maydis*, *Cochliobolus heterostrophus*, *Gloeocercospora sorghi*, *Puccinia polysora*, *Cercospora zeae-maydis*, *Rhizoctonia solani*.

Citrus diseases: *Diaporthe citri*, *Elsinoe fawcetti*, *Penicillium* spl. (*R. digitatum*, *P. italicum*), *Phytophthora parasitica*, *Phytophthora citrophthora*).

Apple diseases: *Monilinia mali*, *Valsa ceratosperma*, *Podosphaera leucotricha*, *Alternaria alternata* apple pathotype, *Venturia inaequalis*, *Colletotrichum acutatum*, *Phytophtora cactorum*.

Pear diseases: *Venturia nashicola*, *Venturia pirina*, *Alternaria alternata* Japanese pear pathotype, *Gymnosporangium haraeanum*, *Phytophtora cactorum*;

Peach diseases: *Monilinia fructicola*, *Cladosporium carpophilum*, *Phomopsis* sp.

Grape diseases: *Elsinoe ampelina*, *Glomerella cingulata*, *Uncinula necator*, *Phakopsora ampelopsidis*, *Guignardia bidwellii*, *Plasmopara viticola*.

Persimmon diseases: *Gloeosporium kaki*, *Cercospora kaki* (*Mycosphaerella nawae*).

Gourd diseases: *Colletotrichum lagenarium*, *Sphaerotheca fuliginea*, *Mycosphaerella melonis*, *Fusarium oxysporum*, *Pseudoperonospora cubensis*, *Phytophthora* sp., *Pythium* sp.;

Tomato diseases: *Alternaria solani*, *Cladosporium fulvum*, *Phytophthora infestans*.

Eggplant diseases: *Phomopsis vexans*, *Erysiphe cichoracearum*.

Brassica family diseases: *Alternaria japonica*, *Cercosporella brassicae*, *Plasmodiophora brassicae*, *Peronospora parasitica*.

Welsh onion diseases: *Puccinia allii*, *Peronospora destructor*.

Soybean diseases: *Cercospora kikuchii*, *Elsinoe glycines*, *Diaporthe phaseolorum* var. *sojae*, *Septoria glycines*, *Cercospora sojina*, *Phakopsora pachyrhizi*, *Phytophthora sojae*, *Rhizoctonia solani*, *Corynespora casiicola*, *Sclerotinia sclerotiorum*.

Kidney bean disease: *Colletotrichum lindemthianum*.

Peanut diseases: *Cercospora personata*, *Cercospora arachidicola*, *Sclerotium rolfsii*.

Pea disease: *Erysiphe pisi*.

Potato diseases: *Alternaria solani*, *Phytophthora infestans*, *Phytophthora erythroseptica*, *Spongospora subterranean* f. sp. *subterranea*.

Strawberry diseases: *Sphaerotheca humuli*, *Glomerella cingulata*.

Tea diseases: *Exobasidium reticulatum*, *Elsinoe leucospila*, *Pestalotiopsis* sp., *Colletotrichum theae-sinensis*.

Tobacco diseases: *Alternaria longipes*, *Erysiphe cichoracearum*, *Colletotrichum tabacum*, *Peronospora tabacina*, *Phytophthora nicotianae*.

Rapeseed diseases: *Sclerotinia sclerotiorum*, *Rhizoctonia solani*.

Cotton disease: *Rhizoctonia solani*.

Sugar beat diseases: *Cercospora beticola*, *Thanatephorus cucumeris*, *Thanatephorus cucumeris*, *Aphanomyces cochlioides*.

Rose diseases: *Diplocarpon rosae*, *Sphaerotheca pannosa*, *Peronospora sparsa*.

Chrysanthemum and asteraceous vegetable diseases: *Bremia lactucae*, *Septoria chrysanthemi-indici*, *Puccinia horiana*.

Diseases of various crops: diseases caused by genus *Pythium* sp. (*Pythium aphanidermatum*, *Pythium debarianum*, *Pythium graminicola*, *Pythium irregulare*, *Pythium ultimum*), *Botrytis cinerea*, *Sclerotinia sclerotiorum*.

Radish disease: *Alternaria brassicicola*.

Zoysia diseases: dollar spot disease (*Sclerotinia homeocarpa*), brown patch disease and large patch disease (*Rhizoctonia solani*).

Banana diseases: *Mycosphaerella fijiensis*, *Mycosphaerella musicola*.

Sunflower disease: *Plasmopara halstedii*.

Seed diseases and diseases at growth initial stage of various crops causes by genus *Aspergillus*, genus *Penicillium*, genus *Fusarium*, genus *Gibberella*, genus *Tricoderma*, genus *Thielaviopsis*, genus *Rhizopus*, genus *Mucor*, genus *Corticium*, genus *Phoma*, genus *Rhizoctonia* and genus *Diplodia* fungi and the like.

Virus diseases of various crops mediated by genus *Polymixa* or genus *Olpidium*, and the like.

Examples of plants on which the inventive compound can be used include the following plants.

Agricultural crops: corn, rice, wheat, barley, rye, oat, sorghum, cotton, soybean, peanut, buckwheat, sugar beet, rapeseed, sunflower, sugar cane, tobacco, etc.;

Vegetables: Solanaceaeous vegetables (eggplant, tomato, green pepper, hot pepper, potato, etc.), Cucurbitaceous vegetables (cucumber, pumpkin, zucchini, watermelon, melon, squash, etc.), Cruciferous vegetables (Japanese radish, turnip, horseradish, kohlrabi, Chinese cabbage, cabbage, brown mustard, broccoli, cauliflower, etc.), Asteraceous vegetables (burdock, garland chrysanthemum, artichoke, lettuce, etc.), Liliaceous vegetables (Welsh onion, onion, garlic, asparagus etc.), Umbelliferous vegetables (carrot, parsley, celery, parsnip, etc.), Chenopodiaceous vegetables (spinach, Swiss chard, etc.), Labiataceous vegetables (Japanese basil, mint, basil, etc.), strawberry, sweat potato, yam, aroid, etc.;

Flowering plants;

Ornamental foliage plants;

Zoysia;

Fruit trees: pome fruits (apple, common pear, Japanese pear, Chinese quince, quince etc.), stone fruits (peach, plum, nectarine, Japanese plum, cherry, apricot, prune etc.), citrus (mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut palm, oil palm, etc.;

Trees other than fruit trees: tea, mulberry, flowering trees, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew), etc.

The above-described plant may also be a plant endowed with a resistance by a genetic engineering technology.

The inventive composition can also be used with other fungicides, insecticides, acaricides, nematicides, herbicides, plant growth regulator, fertilizers or soil improving agents in admixture or simultaneously without mixing.

The method of controlling a plant disease of the present invention (hereinafter, may be referred to as the inventive control method) is carried out by treating a plant or a soil where a plant grows with an effective amount of the inventive composition. Examples of such plants include plant stems and leaves, plant seeds and plant bulbs. Here, the bulb includes a scaly bulb, solid bulb, root stock, stem tuber, root tuber and rhizophere.

In the present control method, examples of the treating method of the inventive composition include a stem and leaf treatment, a soil treatment, a root part treatment and a seed treatment.

Examples of such a stem and leaf treatment include a method of treating the surface of a cultivated plant by spraying on stems and leaves and spraying on the trunk.

Examples of such a root part treatment include a method of immersing the whole body or a root part of a plant into a drug solution containing the present carboxamide compound, and a method of allowing a solid formulation containing the present carboxamide compound and a solid carrier to adhere to a root part of a plant.

Examples of such a soil treatment include spraying on a soil, mixing with a soil and drug solution injection into a soil.

Examples of such a seed treatment include a treatment of seeds or bulb of a plant to be protected from a plant disease with the inventive composition, and specifically a spray treatment of processing a suspension of the inventive composition into a mist and spraying this mist on the surface of a seed or the surface of a bulb, a coating treatment of coating a wettable powder, emulsifiable concentrate or flowable formulation of the inventive composition on a seed or bulb or adding a small amount of water to these formulations and coating a seed or bulb with these formulations, an immersion treatment of immersing seeds into a solution of the inventive composition for a certain time, a film coat treatment and a pellet coat treatment.

The treatment amount of the inventive composition in the inventive control method varies depending on the kind of a plant to be treated, the kind of a plant disease as a control subject, and generation frequency, formulation form, treatment period, treatment method, treatment place, weather conditions and the like, and when stems and leaves of a plant are treated or a soil where a plant grows is treated, it is usually 1 to 500 g, preferably 2 to 200 g, more preferably 10 to 100 g per 1000 m$^2$, in terms of the amount of the present carboxamide compound in the inventive composition. The treatment amount of the inventive composition in the case of treatment of a seed is usually 0.001 to 10 g, preferably 0.01 to 1 g per 1 kg of seeds, in terms of the amount of the present carboxamide compound.

An emulsifiable concentrate, wettable powder, flowable formulation and the like are usually diluted with water and sprayed in treatments. In this case, the concentration of the present carboxamide compound is usually 0.0005 to 2 wt %, preferably 0.005 to 1 wt %. A dust, granule and the like are usually used in treatments without dilution.

EXAMPLES

The present invention will be illustrated further in detail by reference production examples, formulation examples, test examples and the like below.

First, reference production examples of the present carboxamide compound are shown.

Reference Production Example 1

Into a solution composed of 0.15 g of (R)-1,1,3-trimethyl-4-aminoindane (optical purity: 99% ee), 0.13 g of triethylamine, 5 mg of 4-dimethylaminopyridine and 1 mL of THF, a solution of 0.18 g of 1-methyl-3-trifluoromethylpyrazole-4-carbonyl chloride in THF was dropped under ice cool. The mixture was stirred at room temperature for 15 minutes, then, to the reaction mixture was added ice water, and the mixture was extracted with ethyl acetate. The organic layer was washed with a saturated sodium hydrogen carbonate aqueous solution and saturated saline sequentially, then, dried over magnesium sulfate and concentrated under reduced pressure. The resultant residue was subjected to silica gel column chromatography to obtain 0.18 g of (R)-(−)-N-(1,1,3-trimethylindan-4-yl)-1-methyl-3-trifluoromethylpyrazole-4-carboxamide (hereinafter, referred to as present carboxamide compound (1)) (optical purity: 99% ee).

The present carboxamide compound (1)

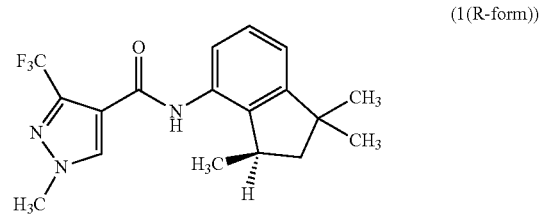 [SMILES: C[C@@H]1CC(C)(C)c2cccc(NC(=O)c3cn(C)nc3C(F)(F)F)c21]

(1(R-form))

$^1$H-NMR (CDCl$_3$) δ: 1.25 (3H, s), 1.28 (3H, d, J=7.1 Hz), 1.34 (3H, s), 1.67 (1H, dd, J=12.8, 4.3 Hz), 2.24 (1H, dd, J=12.9, 8.5 Hz), 3.29-3.37 (1H, m), 3.99 (3H, s), 7.00 (1H, d, J=6.8 Hz), 7.23-7.27 (1H, m), 7.62 (1H, br s), 7.76 (1H, d, J=7.8 Hz), 8.04 (1H, s).
[α]$_D^{23}$=−54° (CHCl$_3$, c1.02)

Reference Production Example 2

Into a solution composed of 0.15 g of (R)-1,1,3-trimethyl-4-aminoindane (optical purity: 99% ee), 0.13 g of triethylamine, 5 mg of 4-dimethylaminopyridine and 1 mL of THF, a solution of 0.17 g of 1-methyl-3-difluoromethylpyrazole-4-carbonyl chloride in THF was dropped under ice cool. The mixture was stirred at room temperature for 15 minutes, then, to the reaction mixture was added ice water, and the mixture was extracted with ethyl acetate. The organic layer was washed with a saturated sodium hydrogen carbonate aqueous solution and saturated saline sequentially, then, dried over magnesium sulfate and concentrated under reduced pressure. The resultant residue was subjected to silica gel column chromatography to obtain 0.20 g of (R)-(−)-N-(1,1,3-trimethylindan-4-yl)-1-methyl-3-difluoromethylpyrazole-4-carboxamide (hereinafter, referred to as present carboxamide compound (2)) (optical purity: 99% ee).

The present carboxamide compound (2)

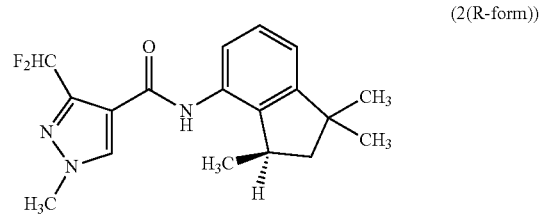 [SMILES: C[C@@H]1CC(C)(C)c2cccc(NC(=O)c3cn(C)nc3C(F)F)c21]

(2(R-form))

$^1$H-NMR (CDCl$_3$) δ: 1.25 (3H, s), 1.28 (3H, d, J=7.1 Hz), 1.34 (3H, s), 1.67 (1H, dd, J=12.9, 4.1 Hz), 2.24 (1H, dd, J=12.9, 8.5 Hz), 3.32-3.41 (1H, m), 3.94 (3H, s), 6.88 (1H, t, J=54.1 Hz), 6.98 (1H, d, J=7.6 Hz), 7.22-7.27 (1H, m), 7.79 (1H, d, J=7.8 Hz), 7.96 (1H, br s), 8.02 (1H, s).
[α]$_D^{23}$=−62° (CHCl$_3$, c0.99)

Reference Production Example 3

Into a solution composed of 0.15 g of (R)-1,1,3-trimethyl-4-aminoindane (optical purity: 99% ee), 0.13 g of triethylamine, 5 mg of 4-dimethylaminopyridine and 1 mL of THF, a solution of 0.15 g of 1,3,5-trimethylpyrazole-4-carbonyl chloride in THF was dropped under ice cool. The mixture was stirred at room temperature for 15 minutes, then, to the reaction mixture was added ice water, and the mixture was extracted with ethyl acetate. The organic layer was washed with a saturated sodium hydrogen carbonate aqueous solution and saturated saline sequentially, then, dried over magnesium sulfate and concentrated under reduced pressure. The resultant residue was subjected to silica gel column chromatography to obtain 0.17 g of (R)-(−)-N-(1,1,3-trimethylindan-4-yl)-1,3,5-trimethylpyrazole-4-carboxamide (hereinafter, referred to as present carboxamide compound (3)) (optical purity: 99% ee).

The present carboxamide compound (3)

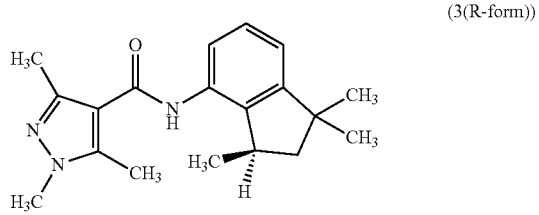 [SMILES: Cc1nn(C)c(C)c1C(=O)Nc1cccc2c1[C@H](C)CC2(C)C]
(3(R-form))

$^1$H-NMR (CDCl$_3$) δ: 1.25 (3H, s), 1.32 (3H, d, J=7.1 Hz), 1.34 (3H, s), 1.67 (1H, dd, J=12.7, 4.6 Hz), 2.24 (1H, dd, J=12.9, 8.5 Hz), 2.51 (3H, s), 2.53 (3H, s), 3.31-3.39 (1H, m), 3.76 (3H, s), 6.96 (1H, d, J=7.6 Hz), 7.21-7.26 (2H, m), 7.76 (1H, d, J=7.8 Hz).

$[α]_D^{23}$=−57° (CHCl$_3$, c1.01)

Next, production of production intermediates of the present carboxamide compounds will be shown.

Reference Production Example 4

Using HPLC, 4.8 g of racemic 1,1,3-trimethyl-4-aminoindane was separated into both enantiomeric isomers under the following conditions, thereby obtaining 1.2 g of (R)-1,1,3-trimethyl-4-aminoindane (optical purity: 99% ee) eluted as a latter peak.

Column: CHIRACEL (registered trademark) OD optically active column
Column temperature: room temperature
Mobile phase: a mixed solvent of hexane and 2-propanol (99:1)
Flow rate: 10 mL/min (R)-1,1,3-trimethyl-4-aminoindane

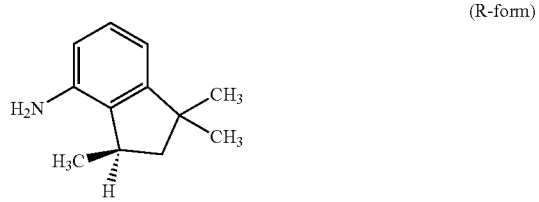
(R-form)

$[α]_D^{25}$=−33.7° (CHCl$_3$, c0.61)

Reference Production Example 5

Three hundred grams (300 g) of racemic 1,1,3-trimethyl-4-aminoindane, 128 g of D-tartaric acid and 260 ml of methanol were mixed, and the mixture was kept at 70° C. for 1 hour. Then, the mixture was left to cool to room temperature, and about 0.1 g of a seed crystal was mixed and the mixture was allowed to stand for 2 days. The generated solid was filtrated off, and washed with methanol. The resultant solid was re-crystallized from methanol five times to obtain 100 g of 1,1,3-trimethyl-4-aminoindane D-tartarate. To 78 g of the resultant 1,1,3-trimethyl-4-aminoindane D-tartarate was added a 5% sodium hydroxide aqueous solution until pH reached 10 or more, and the mixture was extracted with methyl t-butyl ether three times. The resultant oil layers were washed with saturated saline and a saturated sodium hydrogen carbonate aqueous solution sequentially, then, dried over sodium sulfate and concentrated under reduced pressure to obtain 38 g of a mixture of 1,1,3-trimethyl-4-aminoindane in which the enantiomer ratio (R form/S form) was 99.6/0.4.

Next, formulation examples of the inventive composition are shown. Parts are by weight.

Formulation Example 1

Fifty parts (50 parts) of any one compound among the present carboxamide compounds (1) to (3), 3 parts of calcium ligninsulfonate, 2 parts of magnesium laurylsulfate and 45 parts of synthetic hydrated silicon oxide were pulverized and mixed thoroughly to obtain a wettable powder.

Formulation Example 2

Twenty parts (20 parts) of any one compound among the present carboxamide compounds (1) to (3) and 1.5 parts of sorbitan trioleate were mixed with 28.5 parts of an aqueous solution containing 2 parts of polyvinyl alcohol, and the mixture was finely pulverized by a wet pulverization method, then, into this was added 40 parts of an aqueous solution containing 0.05 parts of xanthan gum and 0.1 part of aluminum magnesium silicate, further, 10 parts of propylene glycol was added and stirred to mix, obtaining a formulation.

Formulation Example 3

Two parts (2 parts) of any one compound among the present carboxamide compounds (1) to (3), 88 parts of kaolin clay and 10 parts of talc were pulverized and mixed thoroughly to obtain a dust.

Formulation Example 4

Five parts (5 parts) of any one compound among the present carboxamide compounds (1) to (3), 14 parts of poly-oxyethylene styryl phenyl ether, 6 parts of calcium dodecylbenzenesulfonate and 75 parts of xylene were mixed thoroughly to obtain a formulation.

Formulation Example 5

Two parts (2 parts) of any one compound among the present carboxamide compounds (1) to (3), 1 part of synthetic hydrated silicon oxide, 2 parts of calcium ligninsulfonate, 30 parts of bentonite and 65 parts of kaolin clay were pulverized and mixed thoroughly, then, water was added and the mixture was kneaded thoroughly, and granulated and dried to obtain a granule.

Formulation Example 6

Ten parts (10 parts) of any one compound among the present carboxamide compounds (1) to (3), 35 parts of white carbon containing 50 parts of polyoxyethylene alkyl ether sulfate ammonium salt, and 55 parts of water were mixed, and finely pulverized by a wet pulverization method to obtain a formulation.

The following test examples will show that the inventive composition is useful for control of a plant disease.

The control effect was evaluated by visually observing the area of a lesion on a test plant in investigation, and comparing the area of a lesion on a plant treated with a test composition and the area of a lesion on a non-treated plant.

Test Example 1

Test of Effect of Preventing *Mycosphaerella graminicola* (*Septoria tritici*)

A plastic pot was stuffed with a soil, wheat (variety; Apogee) was sown on this, and allowed to grow in a greenhouse for 10 days. The present carboxamide compounds (1), (2) and (3) were prepared into formulations according to Formulation Example 6, then, the formulations were diluted with water to attain a prescribed concentration (13 ppm), and sprayed to foliar part so as to satisfactorily adhere to the leaf surfaces of the wheat. After spraying, the plant was air-dried, and two days after, inoculated with an aqueous suspension of *Septoria tritici* spores by spraying. After inoculation, the plant was first allowed to stand under humid condition at 18° C. for 3 days, further, allowed to stand for 14 to 18 days under illumination, then, the lesion area was checked. As a result, the lesion on the plant treated with the present carboxamide compounds (1), (2) and (3) was 10% or less of the lesion area on a non-treated plant.

The same test was carried out excepting the application concentration, using racemic N-(1,1,3-trimethylindan-4-yl)-1-methyl-3-trifluoromethylpyrazole-4-carboxylic amide (hereinafter, referred to as racemic compound (A)) instead of the present carboxamide compound. As a result, the lesion area on the plant treated with 50 ppm of the racemic compound (A) was 75% or more of the lesion area on a non-treated plant.

Test Example 2

Test of Effect of Preventing *Puccinia triticina*

A plastic pot was stuffed with a soil, wheat (variety; Shirogane) was sown on this, and allowed to grow in a greenhouse for 10 days. The present carboxamide compounds (1), (2) and (3) were prepared into formulations according to Formulation Example 6, then, the formulations were diluted with water to attain a prescribed concentration (200 ppm), and sprayed to foliar part as to satisfactorily adhere to the leaf surfaces of the wheat. Five days after, the plant was inoculated with *Puccinia triticina* spores by spraying. After inoculation, the plant was allowed to stand under dark humid condition at 18° C. for one day, further, allowed to stand for 9 days under illumination, then, the lesion area was checked. As a result, the lesion area on the plant treated with the present carboxamide compounds (1), (2) and (3) was 10% or less of the lesion area on a non-treated plant.

Test Example 3

Test of Effect of Preventing *Pyrenophora teres*

A plastic pot was stuffed with a soil, barley (variety; Nishinohoshi) was sown on this, and allowed to grow in a greenhouse for 10 days. The present carboxamide compounds (1), (2) and (3) were prepared into formulations according to Formulation Example 6, then, the formulations were diluted with water to attain a prescribed concentration (200 ppm), and sprayed to foliar part so as to satisfactorily adhere to the leaf surfaces of the barley. Five days after, the plant was inoculated with an aqueous suspension of *Pyrenophora teres* spores by spraying. After inoculation, the plant was allowed to stand under humid condition at 23° C. for 3 days, further, allowed to stand for 7 days in greenhouse, then, the lesion area was checked. As a result, the lesion area on the plant treated with the present carboxamide compounds (1), (2) and (3) was 10% or less of the lesion area on a non-treated plant.

Test Example 4

Test of Effect on *Phakopsora pachyrhizi*

A plastic pot was stuffed with a soil, soybean (variety; Natto shoryu) was sown on this, and allowed to grow in a greenhouse until unfolding of the unifoliate. The present carboxamide compound (1) was prepared into formulations according to Formulation Example 6, then, the formulations were diluted with water to attain a prescribed concentration, and sprayed to foliar part so as to satisfactorily adhere to the leaf surfaces of the soybean. The soybean was further cultivated in greenhouse for 14 days, and grown until unfolding of the first trifolidate. The plant was inoculated with an aqueous suspension of *Phakopsora pachyrhizi* spores by spraying. After inoculation, the plant was allowed to stand under humid condition at 23° C. overnight, further, allowed to stand for 7 days at room temperature, then, the lesion area of the first trifoliate was checked.

Based on the lesion areas in the treated plot and the non-treated plot, the effect of the treated plot was calculated according to the following formula (I). The results are shown in [Table 1].

Effect(%)=(1−(lesion area in treated plot)/(lesion area in non-treated plot))×100     formula (1)

TABLE 1

| Test compound | Concentration of test compound [ppm] | Effect [%] |
| --- | --- | --- |
| Present carboxamide (1) | 50 | 98.1 |

Test Example 5

Test of Effect on *Phakopsora pachyrhizi*

A plastic pot was stuffed with a soil, soybean (variety; Natto shoryu) was sown on this, and allowed to grow in a greenhouse until unfolding of the unifoliate. The present carboxamide compounds (2) and (3) and racemic N-(1,1,3-trimethylindan-4-yl)-1-methyl-3-difluoromethylpyrazole-4-carboxamide (hereinafter, referred to as racemic compound (B)) and racemic N-(1,1,3-trimethylindan-4-yl)-1,3,5-trimethylpyrazole-4-carboxamide (hereinafter, referred to as racemic compound (C)) were prepared into formulations according to Formulation Example 6, then, the formulations were diluted with water to attain a prescribed concentration, and sprayed to foliar part so as to satisfactorily adhere to the leaf surfaces of the soybean. The soybean was further cultivated at room temperature for 14 days, and grown until unfolding of the first trifoliate. The plant was inoculated with an aqueous suspension of *Phakopsora pachyrhizi* spores by spraying. After inoculation, the plant was allowed to stand under humid condition at 23° C. overnight, further, allowed to stand for 7 days at room temperature, then, the lesion area of the first trifoliate was checked.

Based on the lesion areas in the treated plot and the non-treated plot, the effect of the treated plot was calculated according to the above-described formula (I). The results are shown in [Table 2].

TABLE 2

| Test compound | Concentration of test compound [ppm] | Effect [%] |
|---|---|---|
| Present carboxamide (2) | 200 | 100 |
| Present carboxamide (2) | 100 | 77.1 |
| Racemic compound (B) | 200 | 46.7 |
| Present carboxamide (3) | 200 | 100 |
| Present carboxamide (3) | 100 | 98.4 |
| Racemic compound (C) | 200 | 76.5 |

INDUSTRIAL APPLICABILITY

According to the present invention, a plant disease can be controlled.

The invention claimed is:

1. A plant disease control composition comprising a carboxamide compound represented by formula (I):

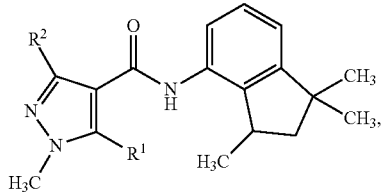

(I)

wherein
$R^1$ represents hydrogen or methyl,
$R^2$ represents methyl, difluoromethyl or trifluoromethyl,
and the enantiomer ratio R form/S form of the carboxamide compound is 80/20 or more.

2. The plant disease control composition according to claim 1, wherein the enantiomer ratio R form/S form of the carboxamide compound is 90/10 to 10000/1.

3. The plant disease control composition according to claim 1, wherein the enantiomer ratio R form/S form of the carboxamide compound is 95/5 to 10000/1.

4. The plant disease control composition according to claim 1, wherein the enantiomer ratio R form/S form of the carboxamide compound is 98/1 to 1000/1.

5. The plant disease control composition according to claim 1, wherein $R^1$ is methyl and $R^2$ is methyl in formula (I).

6. The plant disease control composition according to claim 1, wherein $R^1$ is hydrogen and $R^2$ is difluoromethyl in formula (I).

7. The plant disease control composition according to claim 1, wherein $R^1$ is hydrogen and $R^2$ is trifluoromethyl in formula (I).

8. A method of controlling a plant disease comprising a step of treating a plant or a soil where a plant grows with an effective amount of the plant disease control composition according to claim 1.

9. A carboxamide compound represented by formula (I-R):

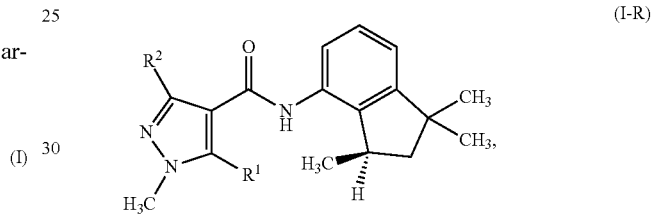

(I-R)

wherein
$R^1$ represents hydrogen or methyl,
$R^2$ represents methyl, difluoromethyl or trifluoromethyl.

10. The carboxamide compound according to claim 9, wherein $R^1$ is methyl and $R^2$ is methyl.

11. The carboxamide compound according to claim 9, wherein $R^1$ is hydrogen and $R^2$ is difluoromethyl.

12. The carboxamide compound according to claim 9, wherein $R^1$ is hydrogen and $R^2$ is trifluoromethyl.

* * * * *